(12) United States Patent
Charlat et al.

(10) Patent No.: US 9,976,937 B2
(45) Date of Patent: May 22, 2018

(54) IMAGE ACQUISITION DEVICE FOR THE VISUAL INSPECTION OF THE INNER SURFACE OF A TIRE, AND ASSOCIATED METHOD

(71) Applicants: COMPAGNIE GENERALE DES ETABLISSEMENTS MICHELIN, Clermont-Ferrand (FR); Michelin Recherche et Technique S.A., Granges-Paccot (CH)

(72) Inventors: Julien Charlat, Clermont-Ferrand (FR); Christian Leobal, Clermont-Ferrand (FR)

(73) Assignee: COMPAGNIE GENERALE DES ETABLISSEMENTS MICHELIN, Clermont-Ferrand (FR)

( * ) Notice: Subject to any disclaimer, the term of this patent is extended or adjusted under 35 U.S.C. 154(b) by 175 days.

(21) Appl. No.: 15/024,597

(22) PCT Filed: Sep. 24, 2014

(86) PCT No.: PCT/EP2014/070358
§ 371 (c)(1),
(2) Date: Mar. 24, 2016

(87) PCT Pub. No.: WO2015/044196
PCT Pub. Date: Apr. 2, 2015

(65) Prior Publication Data
US 2016/0238488 A1    Aug. 18, 2016

(30) Foreign Application Priority Data
Sep. 26, 2013 (FR) ..................... 13 59263

(51) Int. Cl.
*G01M 17/02* (2006.01)
*G01N 21/88* (2006.01)
(Continued)

(52) U.S. Cl.
CPC ...... *G01M 17/027* (2013.01); *G01N 21/8803* (2013.01); *G01N 21/954* (2013.01);
(Continued)

(58) Field of Classification Search
CPC ............ G01M 17/027; G01N 21/8803; G01N 21/954; G06T 7/0004; H04N 5/2252; H04N 5/2256
See application file for complete search history.

(56) References Cited

U.S. PATENT DOCUMENTS 4,392,745 A * 7/1983 Wright ............... B29D 30/0061
356/458
6,840,097 B1 * 1/2005 Huber .................... G01B 11/30
356/237.1
(Continued)

FOREIGN PATENT DOCUMENTS

DE    94 05 098 U1    7/1995
EP    1 959 227 A2    8/2008
(Continued)

*Primary Examiner* — Christopher Findley
(74) *Attorney, Agent, or Firm* — Fitzpatrick, Cella, Harper & Scinto

(57) ABSTRACT

An apparatus for acquiring images of an interior surface of a tire includes at least one image acquisition module. Each image acquisition module is provided with a lighting source, an image acquisition device, and a reflector. The lighting source is arranged to project a beam of light onto a predetermined zone of the interior surface of the tire. The image acquisition device is arranged to acquire a reflected beam of light, which corresponds to light from the beam of light from the lighting source that is reflected off the predetermined zone of the tire. The reflector is positioned optically between the lighting source and the predetermined zone of the tire. Each image acquisition module may be provided with a plurality of lighting sources, image acquisition devices, and reflectors.

12 Claims, 7 Drawing Sheets

(51) Int. Cl.
*G01N 21/954* (2006.01)
*G06T 7/00* (2017.01)
*H04N 5/225* (2006.01)

(52) U.S. Cl.
CPC ......... *G06T 7/0004* (2013.01); *H04N 5/2252* (2013.01); *H04N 5/2256* (2013.01); *G01N 2201/068* (2013.01); *G01N 2201/06113* (2013.01); *G06T 2207/30108* (2013.01)

(56) References Cited

U.S. PATENT DOCUMENTS

| | | | |
|---|---|---|---|
| 7,568,385 B2 | 8/2009 | Maehner et al. | 73/146 |
| 2001/0040682 A1* | 11/2001 | Lindsay | G01B 9/025 356/520 |
| 2005/0264796 A1* | 12/2005 | Shaw | G01B 11/162 356/237.2 |
| 2011/0188052 A1* | 8/2011 | Sotgiu | B60C 25/0554 356/602 |
| 2011/0288814 A1* | 11/2011 | Mizutani | G01B 11/2522 702/150 |
| 2012/0134656 A1 | 5/2012 | Mizukusa et al. | 396/19 |
| 2013/0128029 A1* | 5/2013 | Leobal | G01M 17/021 348/128 |

FOREIGN PATENT DOCUMENTS

| | | |
|---|---|---|
| EP | 2 023 078 A1 | 2/2009 |
| EP | 2 172 737 A1 | 4/2010 |
| EP | 2 431 734 A1 | 3/2012 |

\* cited by examiner

IMAGE ACQUISITION DEVICE FOR THE VISUAL INSPECTION OF THE INNER SURFACE OF A TIRE, AND ASSOCIATED METHOD

FIELD OF THE INVENTION

The present invention relates to the field of the visual inspection of tires.

More particularly, the invention relates to the devices used for acquiring images of the tires so as to carry out the operations of visually inspecting the surfaces thereof.

BACKGROUND

Visual inspection is widely used in the tire manufacturing process and even more commonly relies on the skill of the operators tasked with checking for the absence of visible imperfections at the surface of the tires in order to ensure the compliance thereof.

However, with the advances in the computing power of computer-based means, tire manufacturers are developing automatic inspection means to assist the operators tasked with the visual inspection. To this end, it is possible to use an inspection device comprising lighting means and cameras which are positioned in such a way as to scan the exterior and interior zones of the lateral beads and of the tread of the tire that is to be inspected. The viewing field of each camera is angularly limited. In order to obtain complete images of the inside and of the outside of the tire, the tire has to be turned about its axis with respect to the lighting means and with respect to the cameras. The digital images obtained are then processed and compared against reference images in order to determine whether there might be any surface and appearance anomalies in the tire. For further details, reference may for example be made to patent applications EP-A2-1 959 227, EP-A1-2 023 078 and EP-A1-2 172 737.

In order to carry out such an inspection with a good degree of precision, use is generally made of an image acquisition device equipped with a laser lighting means that allows a line of light to be projected onto the tire and with a matrix camera capable of capturing the light reflected off the tire and which is oriented at a triangulation angle. The triangulation angle is the angle formed between the optical axis of the laser lighting means and the optical axis of the camera.

In order to be able to detect very small imperfections at the surface of the tire, the triangulation angle generally chosen is relatively large. As a result, the overall size of the image acquisition device is large.

Now, in order to be able to capture a complete image of at least half the interior surface of the tire in a single rotation thereof, it is necessary to install a plurality of image acquisition devices penetrating the interior space of the tire.

Given the overall size of each image acquisition device it may therefore be particularly tricky if not to say impossible to achieve this installation for certain tire sizes, for example for tires in the current size range for passenger vehicles.

The present invention seeks to overcome this disadvantage.

BRIEF DESCRIPTION OF THE INVENTION

More specifically, the present invention seeks to provide a device for capturing images of the interior surface of a tire that is restricted in size and suited to be used with tires of different sizes, notably with tires of a diameter less than or equal to 15 inches.

In one embodiment, the device for acquiring images of the interior surface of a tire comprises at least one image acquisition module provided with at least one lighting means able to project a beam of light onto a predetermined zone of the interior surface of the tire, and with at least one image acquisition means able to acquire a beam of light reflected off the said zone of the tire and originating from the projected beam of light and with at least one reflector positioned optically between the lighting means and the predetermined zone of the interior surface of the tire and/or between the said zone of the tire and the image acquisition means, considering the direction of travel of the beam of light.

The use of at least one reflector associated with the projected beam of light and/or with the beam of light reflected off the tire means that the size of that part of the device that is intended to penetrate the interior space of the tire that is to be inspected can be reduced appreciably by folding the said beam(s) of light. The lighting means and/or the image acquisition means may thus be positioned axially outside of this interior space.

It is thus possible to position several image acquisition modules inside the interior space of the tire in a simple and rapid way so that the interior surface of the tire can be visually inspected, even in the case of a small-diameter tire.

According to a first setup option, at least one reflector is positioned optically between the tire and the image acquisition means, the lighting means being positioned and oriented in such a way that the projected beam of light illuminates the tire directly, i.e. without reflection.

According to a second setup option, at least one reflector is positioned optically between the lighting means and the tire, the image acquisition means being positioned and oriented in such a way as to capture directly the beam of light reflected off the tire.

In another arrangement, at least one reflector is interposed optically between the lighting means and the tire, and at least one distinct reflector is interposed optically between the said tire and the image acquisition means.

According to another arrangement, at least one reflector is placed optically both between the lighting means and the tire and between the said tire and the image acquisition means when considering the direction of travel of the beam of light.

For preference, the said acquisition module comprises at least a first reflector positioned optically between the lighting means and the predetermined zone of the interior surface of the tire to reflect the projected beam of light towards the said zone of the tire and at least a second reflector positioned optically between the said zone of the tire and the image acquisition means to reflect the beam of light reflected off the tire towards the said acquisition means. The said reflectors are intended to be situated axially inside the interior space of the tire and the image acquisition means and/or the lighting means are intended to be situated axially outside the said space.

Advantageously, the said acquisition module further comprises a third reflector positioned optically the said zone of the tire and the second reflector so as to reflect the beam of light reflected off the tire towards the said second reflector.

In one embodiment, the device comprises at least first, second and third image acquisition modules. The first and second image acquisition modules may each comprise at least first, second and third reflectors, and the third image acquisition module comprises at least first and second reflectors, the said modules being able to capture half of the interior surface of the tire.

For preference, the acquisition module or modules each comprise a support on which the associated lighting means, the associated image acquisition means and the said associated reflector(s) are mounted. The associated lighting means and image acquisition means may be mounted on opposite faces of the said support.

For preference, the support extends along an axis of elongation substantially parallel to the optical axis of the image acquisition means.

In one preferred embodiment, the said lighting means comprises a laser able to project a line of light onto the predetermined zone of the interior surface of the tire, and the said image acquisition means comprises a matrix camera. The reflector or reflectors may each consist of a folding-optics mirror, preferably planar.

The invention also relates to a method for inspecting a tire of the type comprising a tread and lateral beads, comprising steps during which the tire is rotated about its axis via one of the lateral beads, the other lateral bead of the tire is held at least axially in position during the rotational drive, and images of the interior surface of the tire are captured using an image acquisition device as defined hereinabove. Advantageously, the image acquisition device is positioned on the side of the lateral bead of the tire that is held axially during the rotational drive.

BRIEF DESCRIPTION Of THE DRAWINGS

The present invention will be better understood from reading the detailed description of one embodiment considered by way of entirely nonlimiting example and illustrated by the attached drawings in which.

DETAILED DESCRIPTION OF EMBODIMENTS OF THE INVENTION

Figure 1:
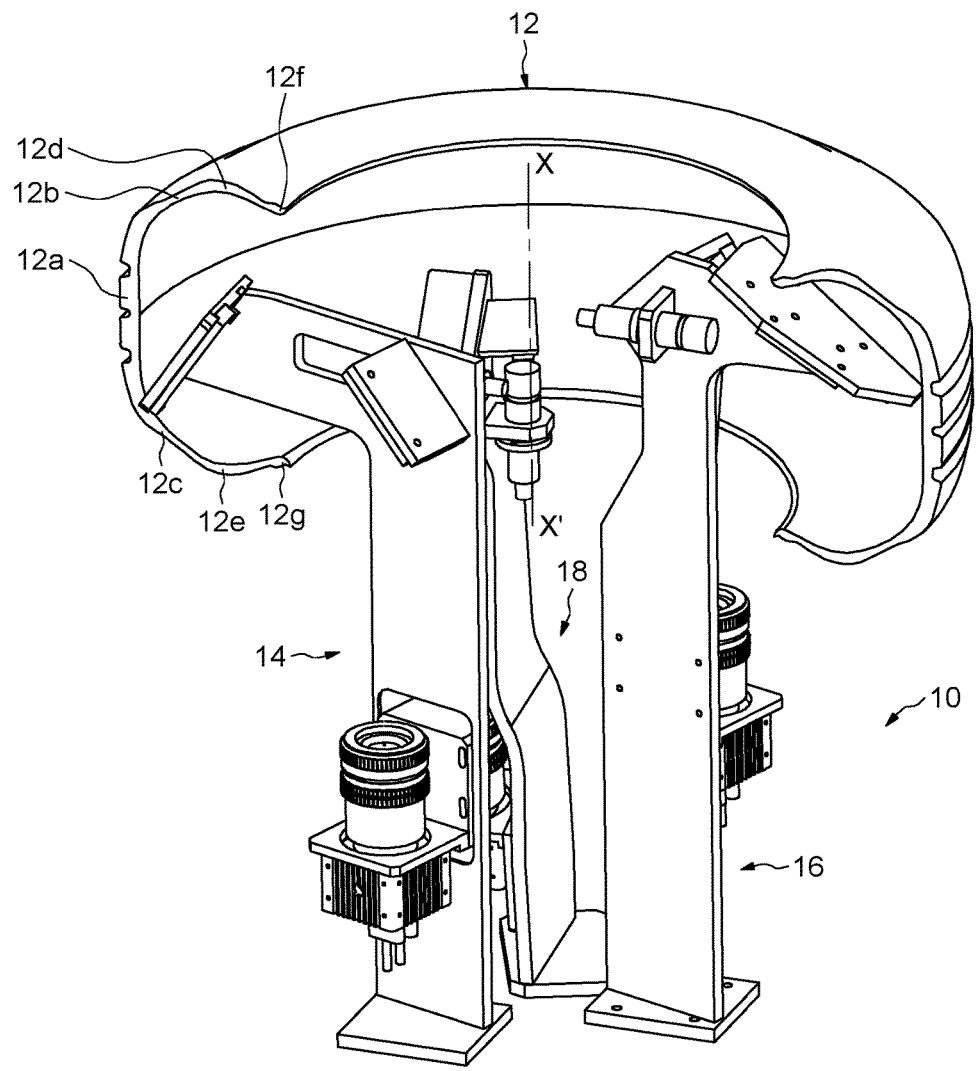
FIG. 1 is a perspective view of an image acquisition device for capturing images of the interior surface of a tire according to one embodiment of the invention.

FIG. 1 depicts one embodiment of a device, referenced 10 overall, intended for capturing images of half of the interior surface of a tire 12 and comprising three acquisition modules 14 to 18.

In the embodiment illustrated, the tire 12, of axis X-X', is depicted in a position in which said axis is assumed to be vertical. The tire 12, of annular shape, comprises a cylindrical tread 12*a* extended by first and second opposing lateral shoulders 12*b*, 12*c* themselves extended by side walls 12*d*, 12*e* then by lateral beads 12*f*, 12*g*. As illustrated, the device 10 allows half of the interior surface of the tire situated between the plane of symmetry of the tire and the lower bead 12*g* to be inspected.

Figure 2:
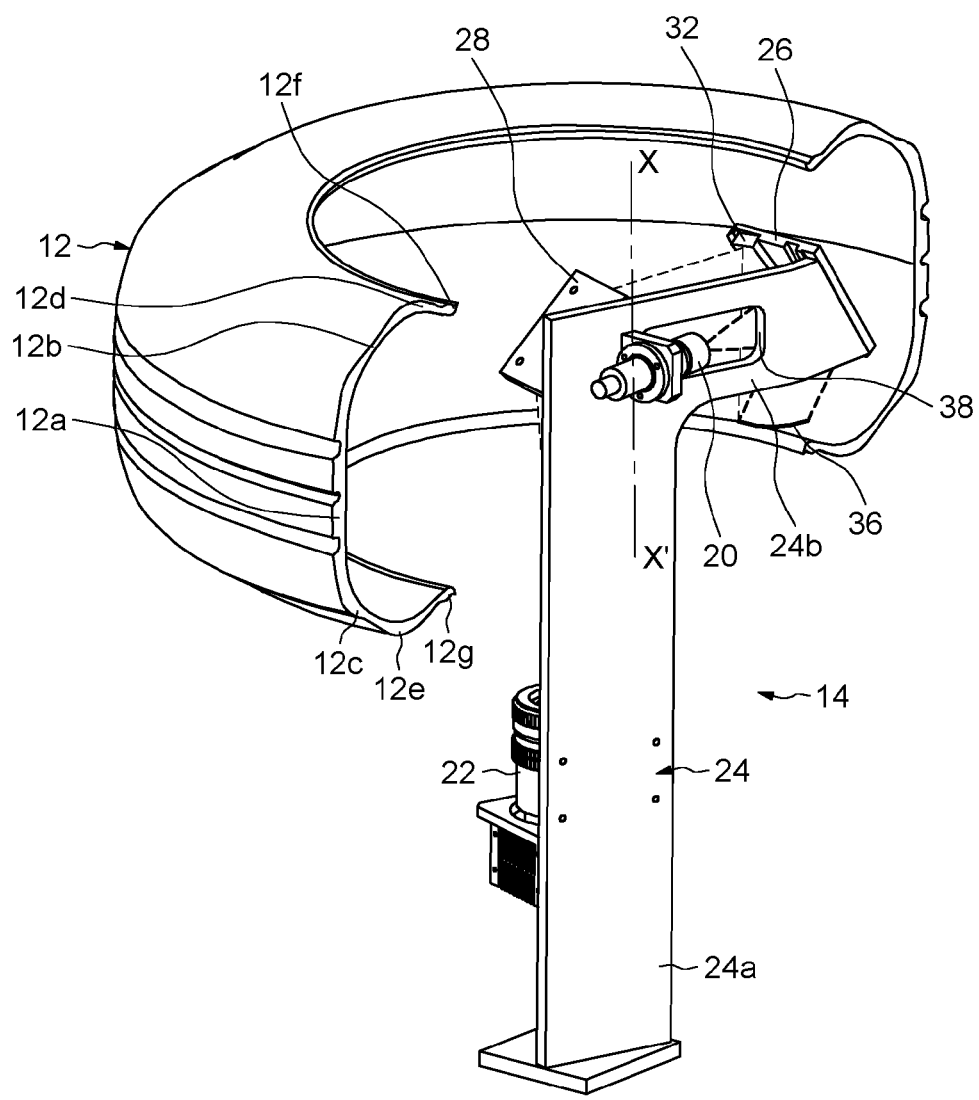
FIGS. 2 and 3 are perspective views of a first acquisition module of the device of FIG. 1, FIGS. 4 and 5 are perspective views of a second acquisition module of the device of FIG. 1, and FIGS. 6 and 7 are perspective views of a third acquisition module of the device of FIG. 1.
Figure 3:
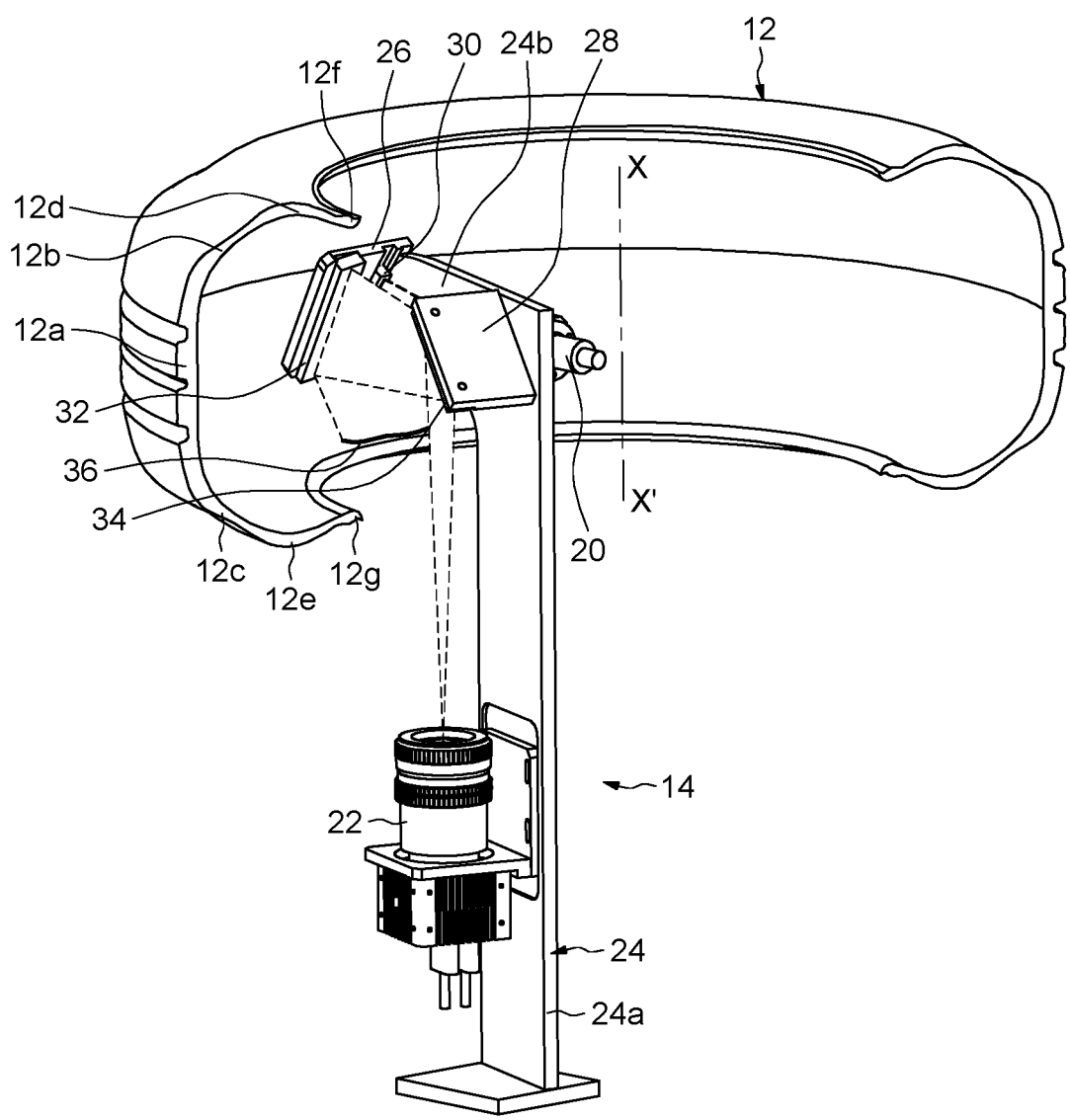

As illustrated more visibly in FIGS. 2 and 3, the first image acquisition module 14 comprises a lighting means 20 for projecting an incident beam of light onto the interior surface of the tire 12, a camera 22 for capturing a beam of light reflected off the said interior surface, and a common support 24 to which the lighting means 20 and the camera 22 are fixed. The lighting means 20 is preferably of the laser type or slot-light type, forming a plane of light of which the intersection with the interior surface of the tire 12 forms a line. The camera 22 is preferably a matrix camera.

The support 24 comprises a main part 24*a* extending along the axis X-X' of the tire and extended at an upper end by a lateral end part 24*b*. The end part 24*b* is situated axially inside the interior space of the tire 12. The lighting means 20 is fixed to the end part 24*b* and the camera 22 is fixed to the main part 24*a* of the support. The lighting means 20 and the camera 22 are fixed to opposite faces of the support 24.

The module 14 also comprises first and second mounting bases 26, 28 positioned on the support 24 and to which mirrors 30 to 34 are fixed. The mounting base 26 is fixed to the free end of the end part 24*b* of the support and extends into the interior space of the tire 12, while remaining radially distant therefrom. The base 26 extends laterally on the side of the base 28 and of the camera 22. The mounting base 28 is fixed in the zone where the end part 24*b* meets the main part 24*a* of the support.

The mirror 30 is fixed to the base 26 and situated axially inside the interior space of the tire 12 and radially between the lighting means 20 and the interior surface of the tire. The mirror 30 is positioned in the optical path of the beam of light which is projected by the lighting means 20 in a substantially radial direction of travel. The mirror 30 is inclined with respect to the optical axis of the lighting means 20 so as to reflect the projected beam of light towards a predetermined zone of the interior surface of the tire 12 which zone is situated on the side wall 12*e* and on the lateral bead 12*g* of the tire. The projected beam of light forms a line 36 on the tire 12. A through-hole 38 is formed in the thickness of the end part 24*b* of the support to allow the incident beam of light to travel towards the mirror 30 which is situated laterally on the opposite side of the support 24 to the lighting means 20.

The mirror 32 is fixed to the mounting base 26 so that it is adjacent to the mirror 30 on the opposite side to the support 24. The mirror 32 is situated axially in the interior space of the tire 12. The beam of light emanating from the lighting means 20 and reflected off the interior surface of the tire 12 illuminates the mirror 32 which reflects the beam inwards towards the mirror 34 in a substantially radial direction of travel. The mirror 34 fixed to the base 28 is positioned in the optical path of the beam of light reflected off the mirror 32 and inclined so as to reflect the said beam towards the camera 22 in a substantially axial direction of travel. The mirror 34 is situated axially inside the interior space of the tire 12 and is radially offset towards the inside with respect to the mirrors 30, 32.

In the exemplary embodiment illustrated, the optical axis of the lighting means 20 is oriented substantially radially when considering the axis X-X' of the tire. The lighting means 20 is situated axially inside the interior space of the tire 12. The mirror 30 is inclined with respect to the optical axis of the lighting means 20 so as to reflect the emitted beam of light onto the side wall 12*e* and onto the bead 12*g* of the tire. Next, the beam of light reflected off the tire 12 heads towards the mirror 32 which is oriented in such a way as to reflect the said beam towards the mirror 34 which reflects the beam towards the camera 22. The optical axis of the objective of the camera 22 extends substantially axially. The camera 22 is situated axially outside of the interior space of the tire 12. The camera 22 in this instance is offset axially downwards with respect to the tire 12. In FIGS. 2 and 3, the projected beam of light and the reflected beams of light are illustrated in dotted line. Two different types of dotted line are illustrated in order to indicate the beams of light before they are reflected off the tire 12 and after reflection.

The second image acquisition module 16 of the device has a structure similar to that of the first module 14. The module 16 is intended to inspect a zone situated on the shoulder 12c and on the side wall 12e of the tire.

Figure 4:
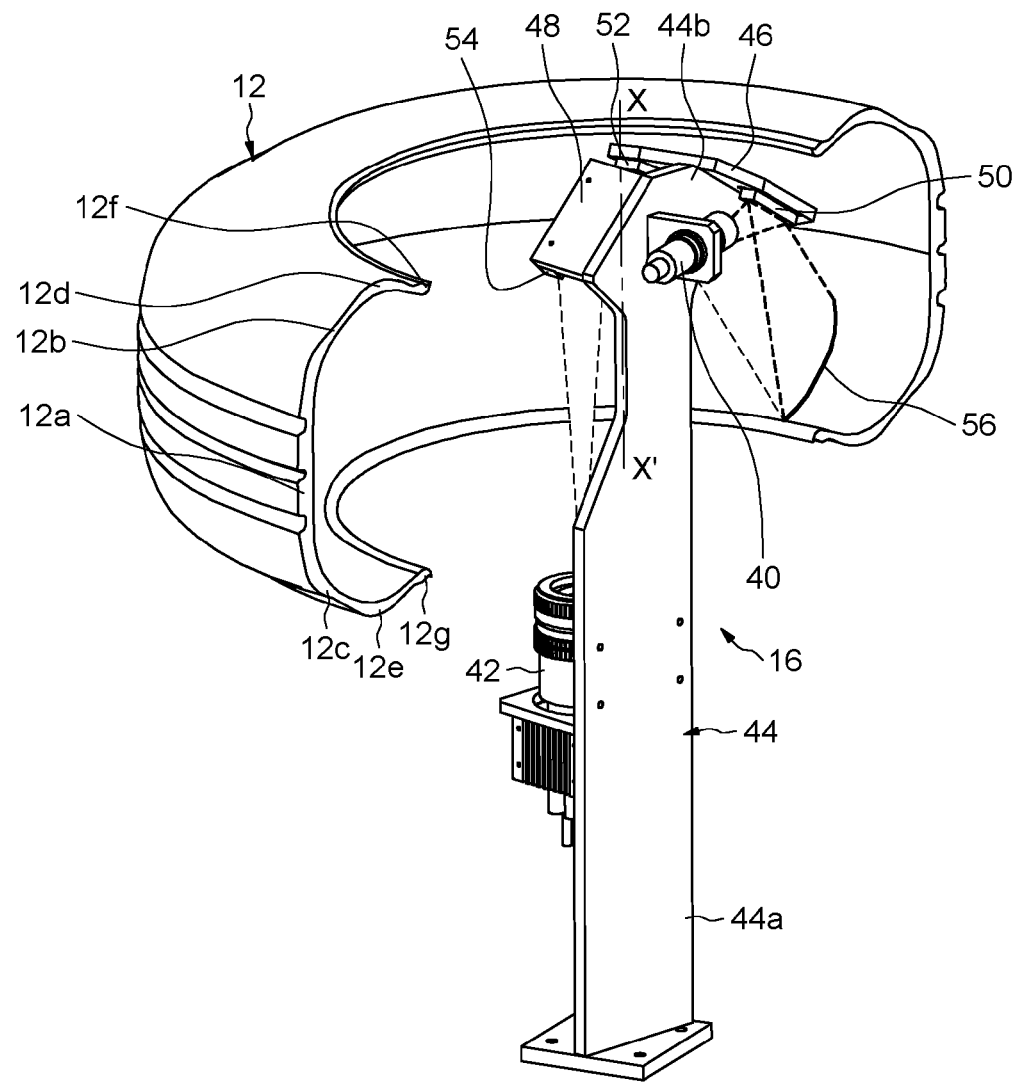
Figure 5:
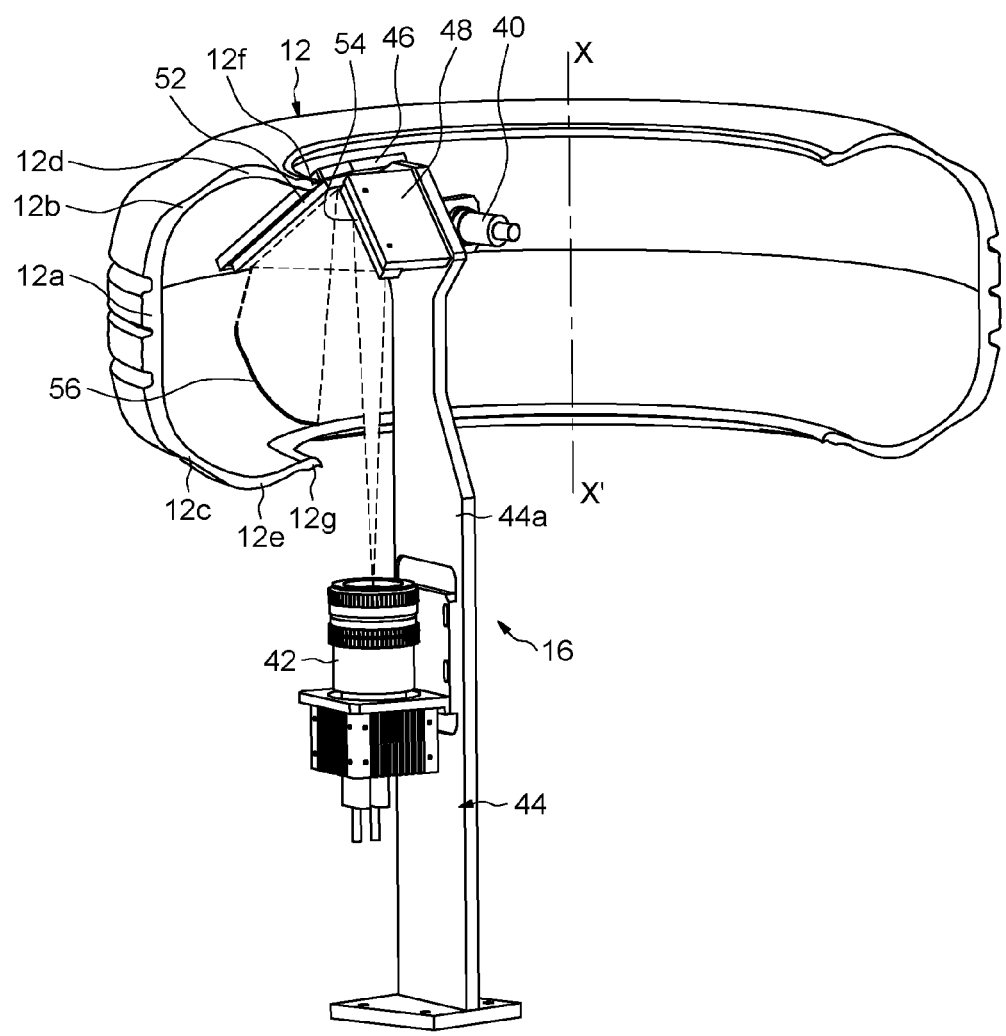

As illustrated in FIGS. 4 and 5, the module 16 comprises a lighting means 40, a camera 42, a common support 44 to which the lighting means 40 and the camera 42 are fixed, first and second mounted bases 46, 48 positioned on the support and to which mirrors 50 to 54 are fixed. The lighting means 40 and the camera 42 are fixed and positioned on the support 44 in an identical way to the lighting means 20 and camera 22 of the image acquisition module 14 described previously. The lighting means 40 is preferably of laser or slot-light type and the camera 42 is preferably a matrix camera.

The mounting base 46 is fixed to the free end of the end part 44b of the support and extends into the interior space of the tire 12, while remaining radially distant therefrom. The base 46 extends laterally on each side of the support 40. In a similar way to the module 14, the mounting base 48 is fixed in the zone where the end part 44b and the main part 44a of the support meet.

The mirror 50 is fixed to the base 46 and situated axially in the interior space of the tire 12 and radially between the lighting means 40 and the interior surface of the tire. The mirror 50 is situated on the same side of the support 44 as the lighting means 40 and is positioned in the optical path of the beam of light projected by the said lighting means in a substantially radial direction of travel. The mirror 50 is inclined with respect to the optical axis of the lighting means 40 so as to reflect the projected beam of light and form a line 56 on the shoulder 12 and on the side wall 12e of the tire. The mirror 52 is fixed to the mounting base 46 on the opposite side of the support 44 to the mirror 50. The mirror 52 is situated axially inside the interior space of the tire 12. The mirror 52 is positioned on the optical path of the beam of light reflected off the tire 12 and in turn reflects the said beam towards the mirror 54 in a substantially radial direction of travel. The mirror 54 is situated axially inside the interior space of the tire 12 while being radially offset towards the inside with respect to the mirrors 50, 52. The beam of light reflected off the mirror 52 is reflected off the mirror 54 towards the camera 42 in a substantially axial direction of travel. The mirror 54 is inclined with respect to the optical axis of the camera 42.

The third image acquisition module 18 of the device is intended for inspecting a zone situated on the tread 12a of the interior surface of the tire. By comparison with the other modules 14 and 16 previously described, the module 18 differs chiefly in that just one reflector is provided for folding the beam of light after it has been reflected off the tire 12.

Figure 6:
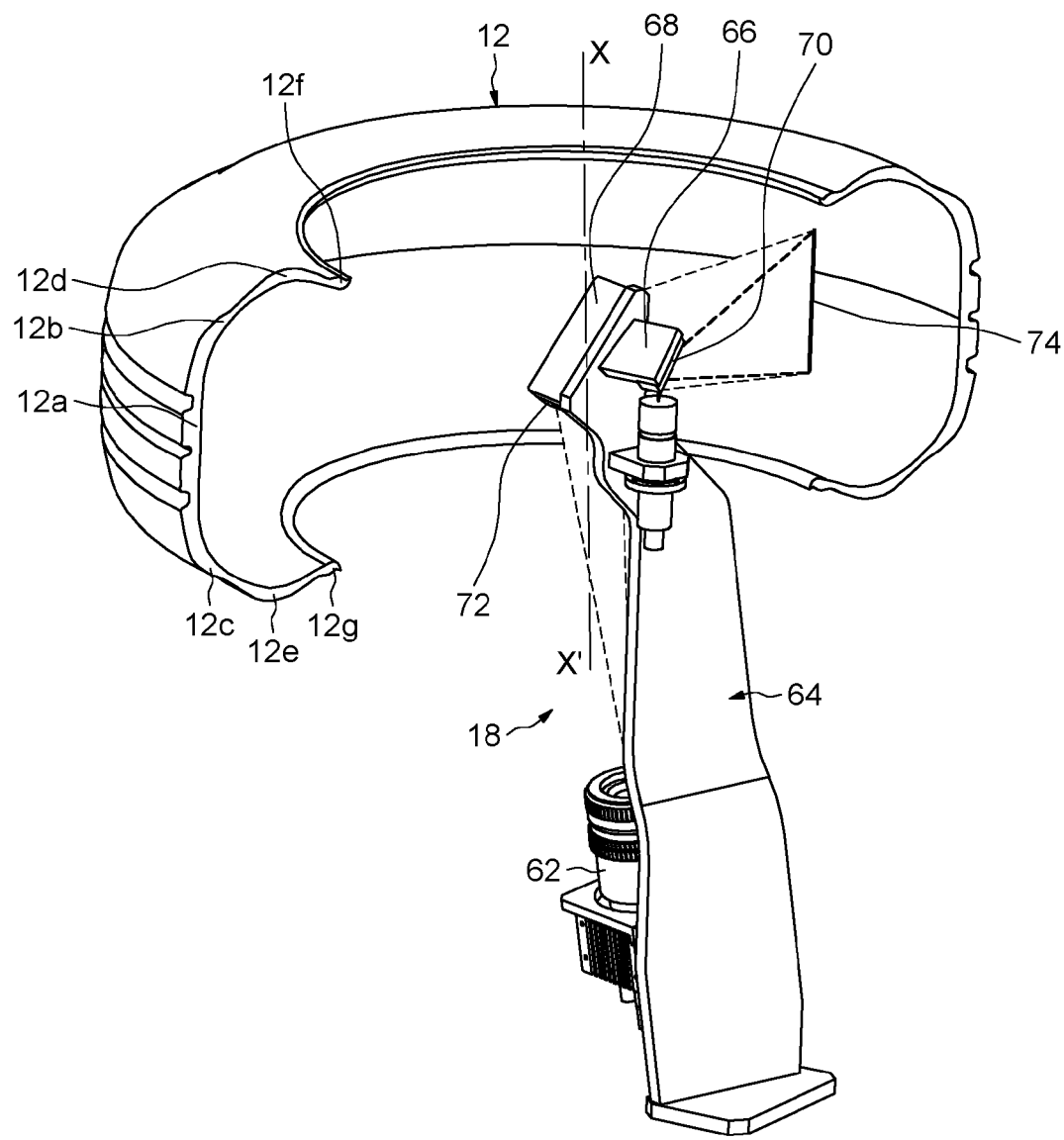
Figure 7:
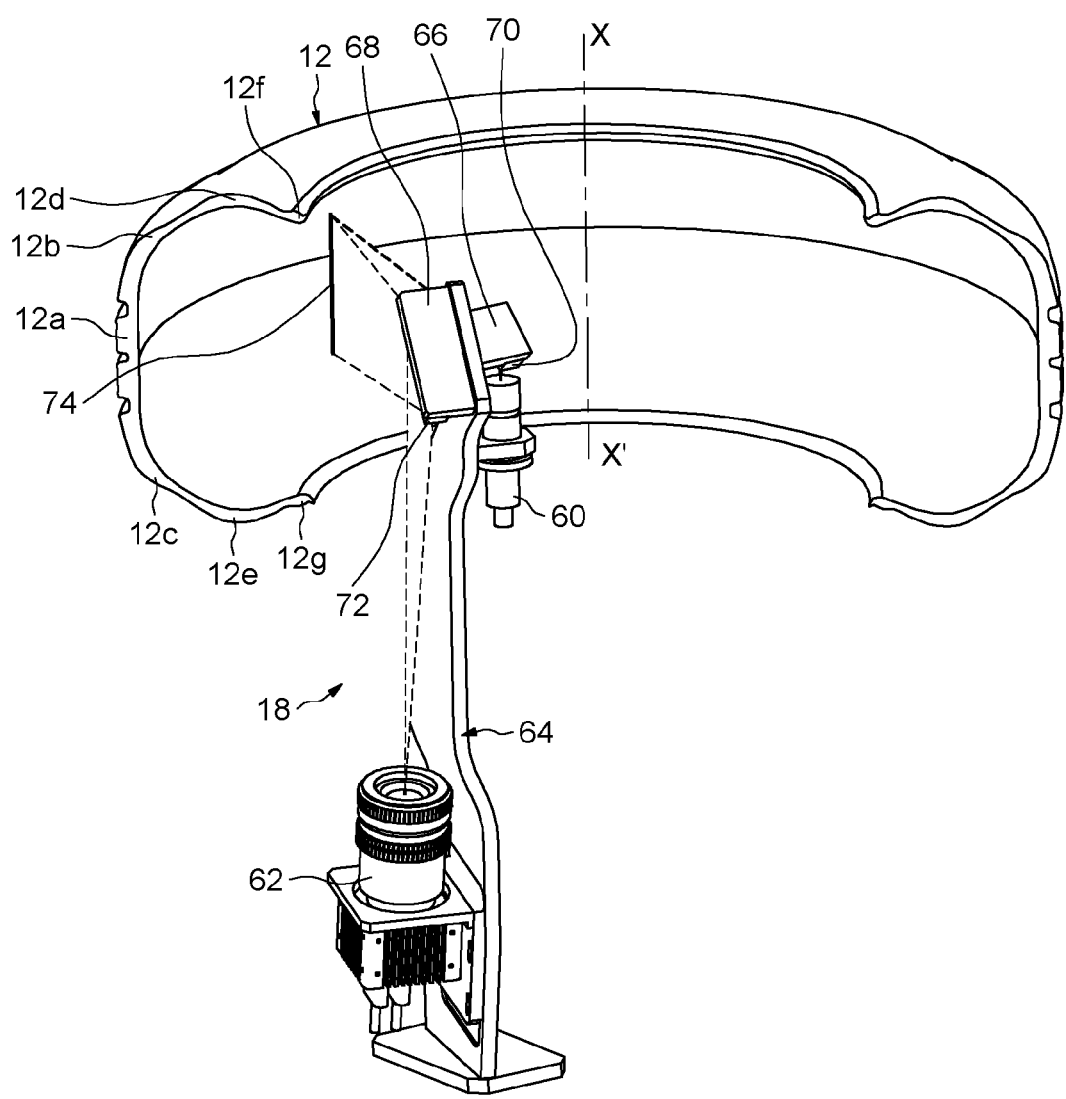

As illustrated in FIGS. 6 and 7, the module 18 comprises a lighting means 60, a camera 62, a common support 64 to which the lighting means 60 and the camera 62 are fixed, first and second mounting bases 66, 68 positioned on the support and to each of which a single mirror 70, 72 is fixed. The camera 62 is fixed and positioned on the support 64 in an identical way to the cameras 22, 42 of the image acquisition modules 14, 16 previously described. The optical axis of the lighting means 60 is oriented substantially axially so as to emit a beam of light in a substantially axial direction of travel. The lighting means 60 is situated axially inside the interior space of the tire 12. The lighting means 60 is preferably of the laser or slot-light type and the camera 62 is preferably a matrix camera.

The mounting bases 66, 68 are fixed near the upper end of the support 64 and extend into the interior space of the tire 12 while remaining radially distant therefrom. The bases 66, 68 are fixed laterally one on each side of the support 64. The mirror 70 is situated axially above the lighting means 60 and is inclined with respect to the optical axis of the said means so as to reflect the projected beam of light in a substantially radial direction of travel and form a line 74 on the tread 12a of the tire. The mirror 72 is situated axially in the interior space of the tire 12 and positioned in the optical path of the beam of light reflected off the tire 12 and in turn reflects the said beam towards the camera 62 in a substantially axial direction of travel. The mirror 72 is inclined with respect to the optical axis of the camera 62.

The device 10 thus comprises three separate modules 14 to 18 each one equipped with at least one folding-optics mirror associated with the lighting means to illuminate a specific zone of the interior surface of the tire 12 and with at least one distinct folding-optics mirror associated with the camera and positioned in such a way that the camera can capture the light reflected off said zone of the tire after it has been reflected off the said mirror. These reflectors respectively allow the beam of light to be folded between, on the one hand, the lighting means and the tire and, on the other hand, the said tire and the camera.

The space occupied by each module 14 to 18 of the device inside the interior space delimited by the tire 12 is limited insofar as the camera of the said module is positioned axially outside of the said space. The modules 14 to 18 can easily be installed in the interior space of the tire 12, even in the case of a relatively small-diameter tire, for example less than or equal to 15 inches. A visual inspection of the lower half of the interior surface of the tire 12 can thus be carried out in a single rotation of the said tire about the axis X-X'.

In order to carry out this inspection using the device 10, the procedure is preferably as follows. In a first step, the first lateral bead 12f of the tire is centred and locked on a means that turns it. Next, in a second step, the second lateral bead 12g is held axially in position for example using a gripper of a type involving rollers. During a subsequent third step, the device 10 is made to partially penetrate the interior space of the tire 12 and is positioned in such a way that the lower half of the interior surface of the tire 12, situated between the plane of symmetry of the said tire and the second bead 12g, can be inspected. Next, in a fourth step, the tire 12 is turned rotationally so that the device 10 which is fixed can capture all of the images that will enable a full image of the lower half of the interior surface of the tire 12 to be formed.

The tire 12 can then be turned over so that the sequence of operations as described hereinabove can be repeated to capture the image of the second half of the interior surface. This then yields a complete image of the interior surface of the tire 12 when the first and second images obtained are juxtaposed. At the same time as obtaining the images of the interior surface of the tire it is possible to capture images of the exterior surface of the tire using another special-purpose image acquisition device.

In the embodiment illustrated, only the camera of each acquisition module is relocated to outside the interior space of the tire. The lighting means and the reflecting mirrors of each acquisition module are situated axially inside the said interior space. As an alternative it is possible also to position the lighting means of each acquisition module axially outside of the interior space of the tire so as to reduce the size of the device in this zone still further. In another alternative form of embodiment it may be conceivable to relocate the lighting means of each module outside of the interior space of the tire 12 and to have the associated camera inside the said space, for example if the camera occupies a small amount of space in comparison with the lighting means.

As indicated previously, in the exemplary embodiment illustrated, each acquisition module of the device comprises at least one mirror situated optically between the lighting means and the tire, and at least one distinct mirror situated optically between the said tire and the image acquisition means. The reflector-forming mirrors are distinct from the tire. As an alternative, it is for example conceivable, without departing from the scope of the present invention, to plan for each acquisition module to have a single mirror associated with the image acquisition means and for the lighting means to be oriented in such a way that the projected beam of light directly illuminates the zone of the interior surface of the tire that is to be inspected. An opposite arrangement could also be considered. In another alternative form of embodiment, it might even be possible, for each acquisition module, to use each mirror both for reflecting the beam emitted by the lighting means and for reflecting the beam reflected off the tire. In that case, the said mirror is interposed optically both between the lighting means and the predetermined zone of the interior surface of the tire, and between the said zone of the tire and the image acquisition means. However, such a solution may be more complicated to implement.

The acquisition device as illustrated in the figures is used in an orientation in which the axis of the tire is vertical. The device may also be used in an orientation in which the axis is horizontal or oblique.

The invention claimed is:

1. An inspection apparatus for a tire, the apparatus comprising:
   at least one image acquisition apparatus structured to acquire images of an interior surface of a tire, wherein each image acquisition apparatus includes:
      a lighting source arranged to project a beam of light onto a predetermined zone of the interior surface of the tire,
      an image acquisition device arranged to acquire a reflected beam of light, and
      at least one reflector positioned optically between the predetermined zone of the interior surface of the tire and the image acquisition device,
   wherein each image acquisition apparatus is arranged relative to a rotation axis of the tire such that the image acquisition device is positioned axially outside the interior space of the tire, and
   wherein the reflected beam of light acquired by the image acquisition device corresponds to light from the beam of light projected from the lighting source that is reflected off the predetermined zone of the interior surface of the tire and that reaches the image acquisition device indirectly via the at least one reflector.

2. The apparatus according to claim 1, wherein the at least one image acquisition apparatus includes a first image acquisition apparatus, a second image acquisition apparatus, and a third image acquisition apparatus.

3. The apparatus according to claim 1, where each image acquisition apparatus includes a support on which an associated lighting source, an associated image acquisition device, and an associated at least one reflector are mounted.

4. The apparatus according to claim 3, wherein the associated lighting source and the associated image acquisition device are mounted on opposite faces of the support.

5. The apparatus according to claim 3, wherein the support extends along an axis of elongation substantially parallel to an optical axis of the associated image acquisition device.

6. The apparatus according to claim 1,
   wherein the lighting source includes a laser arranged to project a line of light onto the predetermined zone of the interior surface of the tire, and
   wherein the image acquisition device includes a matrix camera.

7. The apparatus according to claim 1, wherein each of the at least one reflector includes a folding-optics mirror.

8. An inspection apparatus for a tire, the apparatus comprising:
   at least one image acquisition apparatus structured to acquire images of an interior surface of a tire, wherein each image acquisition apparatus includes:
      a lighting source arranged to project a beam of light onto a predetermined zone of the interior surface of the tire,
      an image acquisition device arranged to acquire a reflected beam of light, the reflected beam of light corresponding to light from the beam of light projected from the lighting source that is reflected off the predetermined zone of the interior surface of the tire, and
      at least one reflector positioned optically between any one or a combination of:
         the lighting source and the predetermined zone of the interior surface of the tire, and
         the predetermined zone of the interior surface of the tire and the image acquisition device,
   wherein the at least one reflector of the image acquisition apparatus includes:
      a first reflector positioned optically between the lighting source and the predetermined zone of the interior surface of the tire, to reflect the beam of light projected from the lighting source towards the predetermined zone of the interior surface of the tire, and
      a second reflector positioned optically between the predetermined zone of the interior surface of the tire and the image acquisition device to reflect the reflected beam of light, which is reflected off the predetermined zone of the interior surface of the tire, towards the image acquisition device,
   wherein the first and second reflectors are arranged axially inside an interior space of the tire, and
   wherein one or both of the image acquisition device and the lighting source is or are arranged axially outside the interior space of the tire.

9. The apparatus according to claim 8, wherein the image acquisition apparatus includes a third reflector positioned optically between the predetermined zone of the interior surface of the tire and the second reflector to reflect the reflected beam of light, which is reflected off the predetermined zone of the interior surface of the tire, towards the second reflector.

10. The apparatus according to claim 9,
   wherein the at least one image acquisition apparatus includes a first image acquisition apparatus, a second image acquisition apparatus, and a third image acquisition apparatus,
   wherein each of the first and second image acquisition apparatuses includes the first, second, and third reflectors, wherein the third image acquisition apparatus includes at least the first and second reflectors, and wherein at least half of the interior surface of the tire is capturable by the first, second, and third image acquisition apparatuses.

11. A method for inspecting an interior surface of a tire of a type that includes a tread and lateral beads, the method comprising steps of:

rotating the tire about an axis of the tire via one of the lateral beads;

holding another of the lateral beads at least axially in position during the rotating step; and capturing images of the interior surface of the tire using an inspection apparatus that includes:
at least one image acquisition apparatus structured to acquire images of an interior surface of a tire, wherein each image acquisition apparatus includes:
a lighting source arranged to project a beam of light onto a predetermined zone of the interior surface of the tire,
an image acquisition device arranged to acquire a reflected beam of light, and
at least one reflector positioned optically between the predetermined zone of the interior surface of the tire and the image acquisition device,
wherein each image acquisition apparatus is arranged relative to a rotation axis of the tire such that the image acquisition device is positioned axially outside the interior space of the tire, and
wherein the reflected beam of light acquired by the image acquisition device corresponds to light from the beam of light projected from the lighting source that is reflected off the predetermined zone of the interior surface of the tire and that reaches the image acquisition device indirectly via the at least one reflector.

12. The method according to claim 11, wherein, in the capturing step, the inspection apparatus is positioned on a side corresponding to the lateral bead of the tire that is held in position at least axially during the rotating step.

* * * * *